(12) United States Patent
Ranke

(10) Patent No.: US 7,041,450 B2
(45) Date of Patent: May 9, 2006

(54) METHOD FOR DIAGNOSING GH DEFICIENCY

(75) Inventor: Michael Ranke, Tübingen (DE)

(73) Assignee: Pharmacia AB, Uppsala (SE)

( * ) Notice: Subject to any disclaimer, the term of this patent is extended or adjusted under 35 U.S.C. 154(b) by 520 days.

(21) Appl. No.: 10/137,578

(22) Filed: May 2, 2002

(65) Prior Publication Data

US 2003/0027185 A1   Feb. 6, 2003

Related U.S. Application Data

(60) Provisional application No. 60/288,190, filed on May 2, 2001.

(30) Foreign Application Priority Data

May 2, 2001   (SE)   ................... 0101532

(51) Int. Cl.
*C12Q 1/68* (2006.01)
*C12P 19/34* (2006.01)
*C07H 21/02* (2006.01)
*C07H 21/04* (2006.01)

(52) U.S. Cl. ................. 435/6; 435/91.1; 435/91.2; 536/23.1; 536/23.5; 536/24.31; 536/24.33

(58) Field of Classification Search .............. 435/6, 435/4.1, 91.1, 91.2; 536/23.1, 23.5, 24.31, 536/24.33
See application file for complete search history.

(56) References Cited

OTHER PUBLICATIONS

Lucentini, J. The Scientist. Dec. 2004, p. 20.*
Wajnrajach et al, *Pathophysiology of Autosomal Dominant GH Deficiency,* Programs and Abstracts from the 79th Annual Meeting of The Endocrine Society, Minneapolis, MN, Abstract PI-84, p. 155 (1997).
Pfäffle et al, *Horm. Res.,* 53(Suppl 3):1-8(2000).
Phillips et al, *Proc. Natl. Acad. Sci. USA,* 78:6372-6375 (1981).
Wajnrajch et al, *Nature Genetics,* 12:88-90 (1996).
Cogan et al, *Journal of Clinical Endocrinology and Metabolism,* 76(5):1224-1228 (1993).
Binder et al, *Journal of Clinical Endocrinology and Metabolism,* 80(4):1247-1252 (1995).
Wagner et al, *Pediatric Research,* 43(1):105-110 (1998).
Binder et al, *Journal of Clinical Endocrinology and Metabolism,* 81(11): 4047-4050 (1996).
Hayashi et al, *Journal of Clinical Endocrinology and Metabolism,* 84(6):2134-2139 (1999).
Lee et al, *Endocrinology,* 14(3):883-890 (2000).
Cogan et al, *Journal of Clinical Endocrinology and Metabolism,* 80(12):3591-3595 (1995).
Cogan et al, *Human Molecular Genetics,* 6(6):909-912 (1997).
Missarelli et al, *Human Genetics,* 101:113-117 (1997).
Hayashi et al, *Growth Hormone and IGF Research,* 9:434-437 (1999).
McCarthy et al, *Human Molecular Genetics,* 7(9):1491-1496 (1998).
Duquesnov et al, *Familial isolated growth hormone deficiency with slight height reduction due to a heterozygote mutation in GH gene,* (Abstract), Proc. 80th Meeting of The Endocrine Society, P2-202 (1998).
Massa et al, *Eur. J. Pediatr.,* 157:272-275 (1998).
Blum et al, *Journal of Clinical Endocrinology and Metabolism,* 76(6): 1610-1616 (1993).
Chomczynski et al, *Analytical Biochemistry,* 162:156-159 (1987).
Chen et al, *Genomics,* 4:479-797 (1989).
Watakabe et al, *Genes & Development,* 7:407-418 (1993).
Prader et al, *Helv. Paediat. Acta. (Suppl.),* 43:3-125 (1998).
Argyropoulou et al, *Pediatric Radiologyi,* 21:247-249 (1991).
Danies, *Vitamins and Hormones,* 58:1-26 (2000).
Cooper et al, *The Metabolic and Molecular Bases of Inherited Disease,* 7th Edition, New York: McGraw-Hill, pp. 259-291, undated.
Ultsch et al, *J. Med. Biol.,* 236:286-299 (1994).
Woods et al, *Balliere's Clinical Endocrinology and Metabolism,* 10(3):371-383 (1996).
Murray et al, *Am. J. Neuroadiol.,* 21:685-689 (2000).
Thorner et al, *William's Textbook of Endocrinology,* 9:249-340 (1998).
Hamilton et al, *Am. J. Neuroadiol.,* 19:1609-1615 (1998).
Zucchini et al, *Journal of Pediatric Endocrinology & Metabolism,* 9:545-548 (1996).

* cited by examiner (Continued)

*Primary Examiner*—Carla J. Myers
(74) *Attorney, Agent, or Firm*—Dinsmore & Shohl LLP

(57) ABSTRACT

The present invention relates to a method and kit for diagnosing GH (growth hormone) deficiency, in particular isolated growth hormone deficiency II (IGHD II). The method comprises the steps of analysing the missense mutation $G^{6191}$ to T in exon 4 of GH-1 which changes valine 110 to phenylalanine.

17 Claims, 6 Drawing Sheets

FIG. 5

|          | 104      | 110       | 115       |
|----------|----------|-----------|-----------|
| Human    | G A S D S N | V Y D   | L L K D L |
| Rat      | G T S D R * | V Y E   | K L K D L |
| Ovine    | G T S D L * | V Y E   | K L K D L |
| Porcine  | G T S D R * | V Y E   | K L K D L |
| Bovine   | G T S D R * | V Y E   | K L K D L |
| Chicken  | G T S D R * | V F E   | K L K D L |
| Bullfrog | G N I D R * | V Y D   | R L R D L |

Third α-Helix →

METHOD FOR DIAGNOSING GH DEFICIENCY

This application claims priority to U.S. Provisional Application No. 60/288,190, filed May 02, 2001.

FIELD OF THE INVENTION

The present invention relates to a method and kit for diagnosing GH (growth hormone) deficiency, in particular isolated growth hormone deficiency II (IGHD II).

BACKGROUND OF THE INVENTION

The majority of cases with isolated growth hormone deficiency (IGHD) are idiopathic (1). Monogenetic recessive inheritance of IGHD was shown to be caused by complete deletions of the GH-1 (IGHD IA)(2) and, more recently, by nonsense mutations of the GHRH receptor gene (3). Dominant transmission (IGHD II) was exclusively found in the presence of GH-1 splice site mutations which cause skipping of exon 3 (4,5). This in-frame deletion results in the loss of 40 amino acids and a presumably misfolded del32-71 GH. The prevalence of such mutations in families with IGHD II is high, up to 100% (6). The mechanism of the dominant negative effect of the mutant protein in only partly understood (7). In-vitro studies suggested cell-specific mechanisms in neuro-endocrine cells which included insufficient storage and secretion of the wild-type GH in the presence of the del32-71GH (8,9). Seven different splice site mutations in intron 3 of GH-1 have been reported (4,5,10–13). Because of the very compact gene structure of the GH-1, splicing is also affected by point mutations outside the conserved splicing sites (14). In addition, two GH-1 missense mutation (P89L and R183H) were recently implicated in IGHD II (15,16).

SUMMARY OF THE INVENTION

The present invention provides novel markers for the diagnosing IGHD II. These markers provide early and accurate diagnosis of affected children. The present inventors have found that not only splice site mutations causing skipping of exon 3 of GH-1 but also GH-1 missense mutations result in a mutant GH with a dominant negative effect. Thus it is very important to also investigate children with suspected GH-deficiency for missense mutations.

In a first aspect, the invention relates to a method for diagnosis of autosomal dominantly inherited isolated GH deficiency (IGHD II) in a patient sample, comprising in vitro analysing the presence or absence of the novel missense mutation $G^{6191}$ to T in exon 4 of GH-1 which changes valine 110 to phenylalanine. Preferably, the method also comprises analysing the presence or absence of GH-1 splice site mutations causing skipping of exon 3 of GH-1. In one preferred embodiment the splice site mutation is the novel +2T to C transition of the second base of the intron 3 donor splice site. Thus, the present invention provides two novel disease markers for IGHD II.

The method of the invention preferably comprises amplification of the GH-1 gene of the patient or fragments derived from the GH-1 gene. Preferably, the intron 3 and/or exon 2–5 are amplified. In a preferred embodiment, the method comprises PCR amplification of the GH-1 gene of the patient and nested PCR of overlapping constituent fragments of the GH-1 gene of the patient. The amplified fragments may be restriction enzyme digested or directly sequenced for detection of said mutations.

In a second aspect, the invention provides a kit for diagnosis of autosomal dominantly inherited isolated GH deficiency (IGHD II) in a patient sample, comprising means for analysing the presence of absence of the missense mutation is $G^{6191}$ to T in exon 4 of GH-1 which changes valine 110 to phenylalanine.

The means may comprise reagents, primers etc for analysing a part of the GH-1 gene which includes this single nucleotide polymorphism. Preferably, the kit also comprises means for analysing the presence or absence of GH-1 splice site mutations causing skipping of exon 3 of GH-1. The splice site mutation is preferably a +2T to C transition of the second base of the intron 3 donor splice site.

The kit of the invention may comprise one or more specific GH-1 primer pairs selected from GH3.2 (nt 6578–6600), GH5.1 (nt 5503–5525); GH5.2 (nt 5555–5577), GH3.4 (nt 6547–6568); GH5.7 (nt 581–5835), GH3.7 (nt 6121–6140) and the following sequencing primers GS5.8 (nt 5629–5648), GS3.8 (6495–6515). Alternatively to the sequencing primers, the kit may comprise one or more of the following restriction enzymes MvnII, N1aIII, DdeI, MaeII.

Autosomal dominantly inherited isolated GH deficiency (IGHD II) is caused by mutations of GH-1 which alter the normal structure of GH. We studied 16 familial cases and one sporadic case with IGHD II from one Dutch and 4 German families by direct sequencing of PCR amplified gDNA and ectopic transcript analysis of lymphocyte mRNA. In addition, the clincal data of the affected individuals were analyzed. Two previously reported mutations and one novel splice site mutation in intron III of GH-1 (+1G to C, +1G to A and new: +2T to C) were detected which cause exon 3 skipping. We also discovered a novel $G^{6191}$ to T missense mutation in exon 4 of GH-1 which changes valine 110 which is highly conserved in mammalian and several non-mammalian GH to phenylalanine. Splicing of the primary RNA transcript was not affected by this mutation which is very likely to alter the normal GH structure at the protein level.

The onset of growth failure was earlier and the degree more severe in the affected children with GH-1 splice site mutations in comparison to those with the GH-1 missense mutation. In addition, the severity of the phenotype was inter-individually very variable, even within the same family. The age at diagnosis was between 0.8 and 9.6 years (median 5.1), height at diagnosis was between −2.5 and −8.1 SDscore (median −4.0). Most of the children were lean at diagnosis with a BMI ranging from −1.7 to +3.3 SDscore (median −0.4). The 5 affected adults had final heights between −1.8 and −4.5 SDscore (median −3.6), centripetal obesity and muscular hypotrophy. Before therapy, IGF-I and IGFBP3 serum levels of all affected children were severely diminished (median IGF I 15.1 µg/L, median IGFBP3 910 µg/L). The maximum GH peak in a total of 25 stimulation tests was between 0.1 and 5.0 µg/L (median 0.9) indicating severe GH deficiency. The height of the adenohypophysis studied by MRI was normal in 2 affected children and mildly decreased in 2 others. Substitution with GH resulted in good catch-up growth in all treated children. The discrepancy between the very homogeneous hormone data proving severe GH- and IGF-I deficiency and the high variability of growth failure, even within the same family, suggests that the onset and the predominance of growth hormone dependent growth during infancy is individually different. Children with severe GH- and IGFI deficiency, but normal size of the adenohypophysis should be examined for GH-1 splice site and missense mutations.

BRIEF DESCRIPTION OF THE DRAWINGS

The invention will be described more closely below in association with the accompanying drawings, in which:

FIG. 5 shows alignment of the human GH sequence (amino acids 104–117) with the sequences from mammalian and non-mammalian GHs. The valine at position 110 is highly conserved and is located next to the N-terminal beginning of the third α-helix. With reference to FIG. 5, the following sequences are disclosed: human (SEQ ID NO: 1), rat (SEQ ID NO: 2), ovine (SEQ TD NO: 3), porcine (SEQ IID NO: 4), bovine (SEQ ID NO: 5), chicken (SEQ lID NO: 6), and bullfrog (SEQ ID NO: 7).

DETAILED DESCRIPTION OF THE INVENTION

Figure 1:
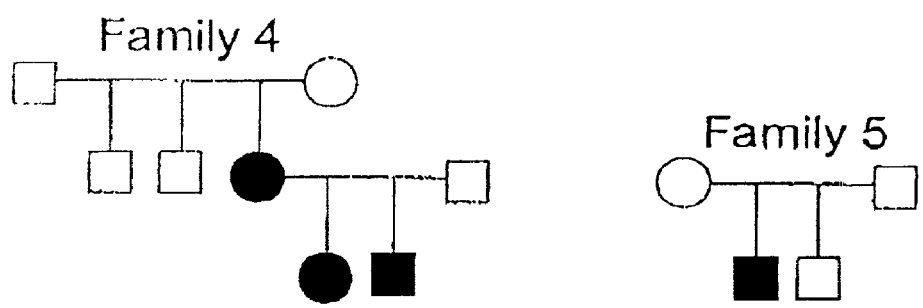
FIG. 1 shows predigrees of the previously reported Families 4 and 5. Filled symbols indicate the affected individuals.
Figure 2:
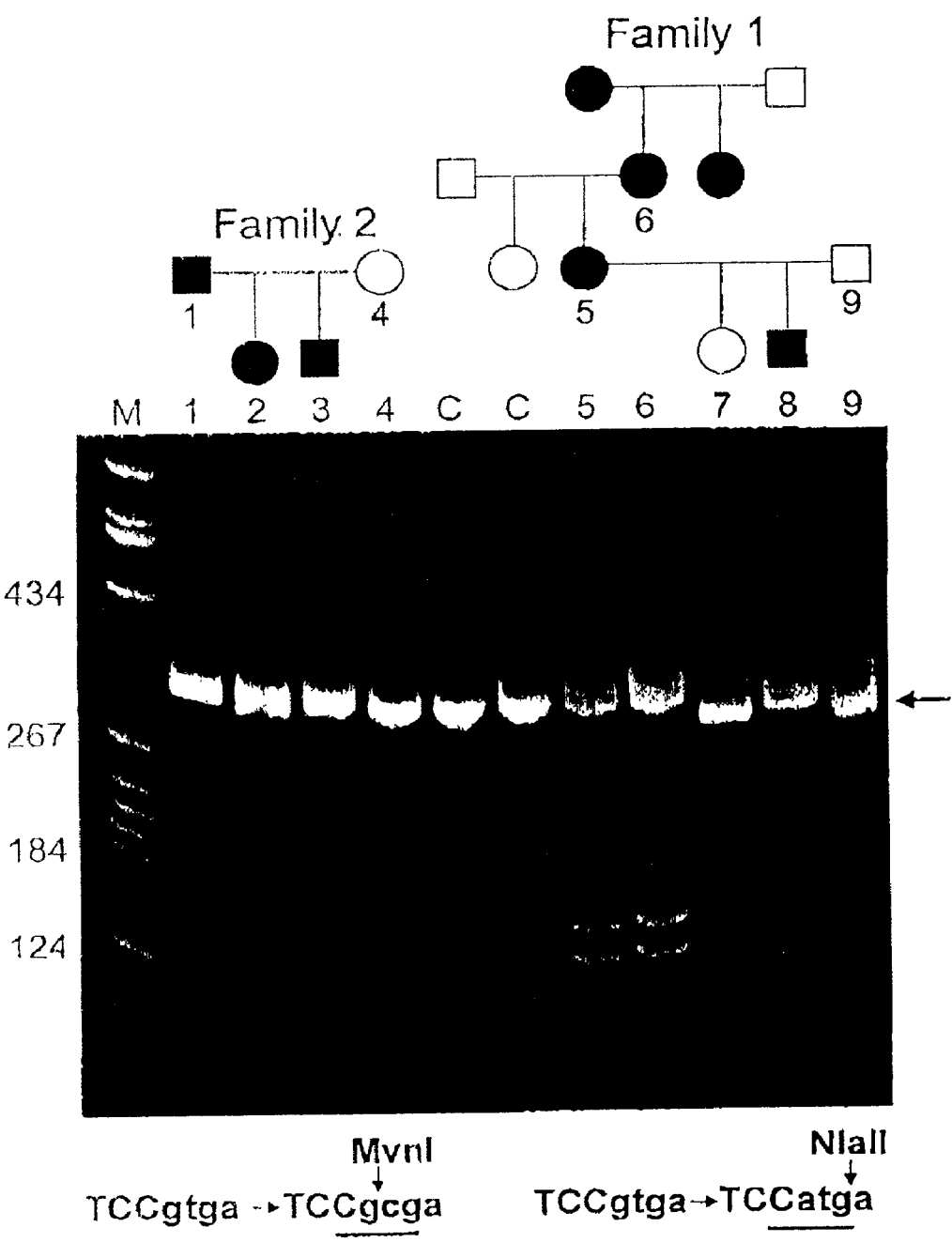
FIG. 2 shows pedigrees of Families 1 and 2 and electrophoretic analysis of the amplified GH-1 fragment from family members (1–9) and normal controls (C) after restriction enzyme digestion with MvnI (Family 2) or N1aII (Family 1) whose recognition sites are underlined below. The band of the undigested fragment is indicated by the arrow. Both heterozygote splice site mutations generate one new recognition site for the respective enzyme which is evident by the appearance of two smaller bands after digestion. M=mol wt marker.
Figure 3:
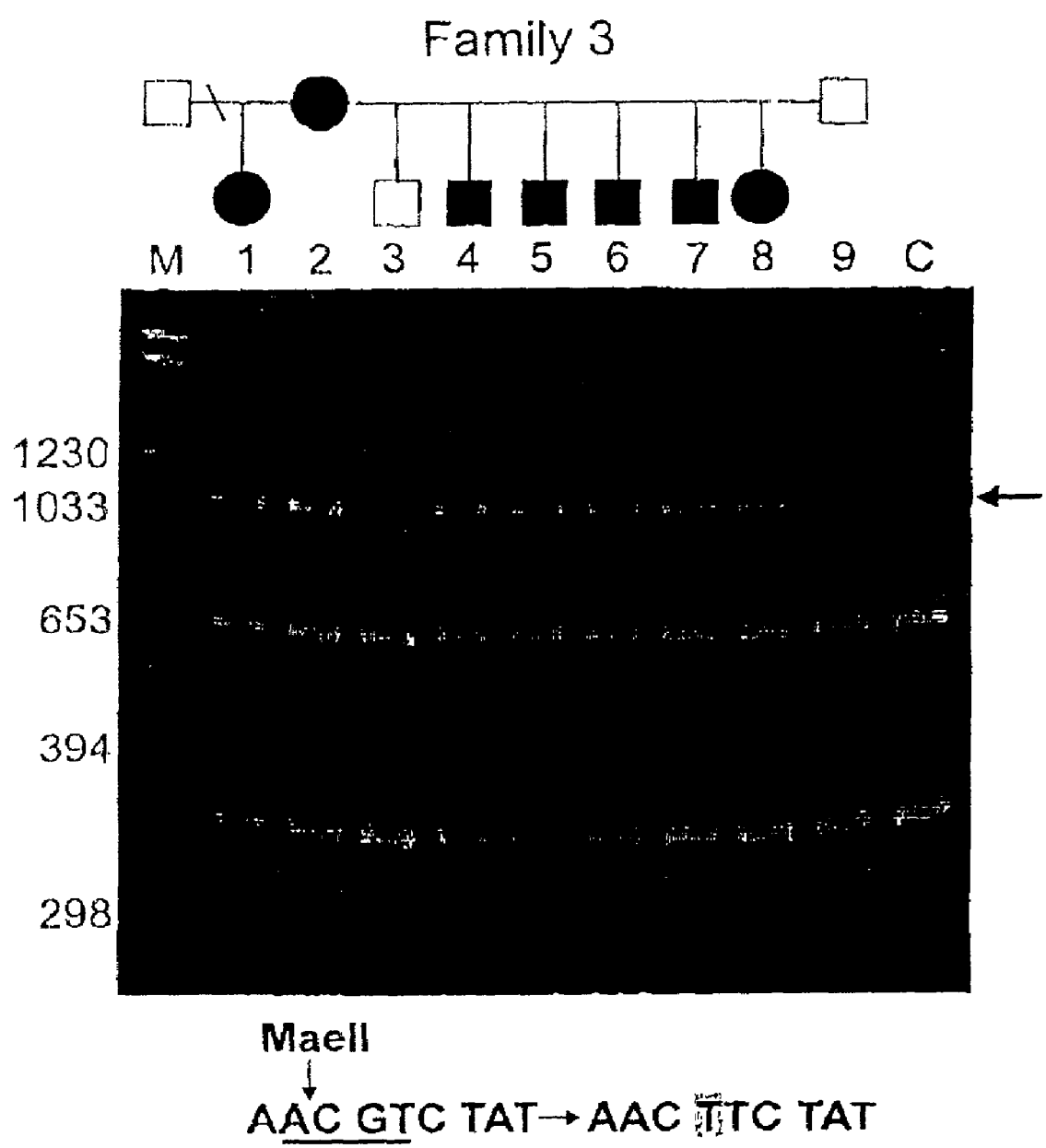
FIG. 3 shows a pedigree of Family 3 nd electrophoretic analysis of the amplified GH-1 fragment from family members (1–9) and one normal control (C) after restriction enzyme digestion with MaeII whose recognition site is underlined below. The band of the undigested fragment is indicated by the arrow. Because the heterozygote mutation destroys the recognition site for MaeII, the DNA fragment of the affected family members is incompletely digested. M=mol wt marker.

The pedigrees of the five families (No. 1 to 5) are shown in FIGS. 1, 2 and 3. Family 4 and Family 5 have been reported previously (5,17). All affected children were prepubertal at diagnosis and had normal fT4, TSH, prolactin and cortisol levels. Basal serum levels of IGF-1 and IGFBP3 were determined in all but one patient. Two independent GH stimulation tests were performed in 7 patients, only the insulin test in 3 patients and no test because of young age (<1.0 year) in 2 patients of which one had a pathologically low GH level during spontaneous hypoglycemia. Out of the 12 affected children, 11 were treated with rhGH sc (median dose 0.17 mg/kg per week). MR imaging with narrow scanning of the pituitary region and gadolinium injection was performed in 4 patients and one affected parent from 3 families. Blood samples for genetic analysis were taken after obtaining informed consent form parents and patients.

Materials and Methids

Hormone Measurements

GH serum levels were measured in different clinical centers by several assays (RIA, ELISA, EIA) which had the same cut-off level of 10 µg GH/L for the normal response to stimulation. IGF-I and IGFBP3 concentrations in Families 1, 2, 3 and 5 were determined using the same assays by Blum et al. (18).

DNA and RNA Extraction

Genomic DNA was extracted from 5 ml frozen EDTA blood using an extraction kit (Genomix Blood Scale-Up, Talent, Triest, Italy) which was based on chloroform extraction after initial blood lysis. Total RNA from peripheral lymphocytes was extracted according to the method described by Chomozynski and Sacchi (19).

Oligonucleotide Primers

For the reverse transcription reaction, the used primer corresponded to nucleotides 6578–6600 (GH3.2) of the reported GH-1 sequence (20). The PCR was performed using GH3.2 and the upstream primer 5503–5525 (GH5.1). The up-stream primer of the nested PCR corresponded to the nucleotides 5555–5577 (GH5.2) and the down-stream primer to 6547–6568 (GH3.4). For restriction digest analysis with MvnII, N1aIII and DdeI, the nested PCR was performed with the upstream primer GH5.7 (5816–5835) and the downstream-primer GH3.7 (6121–6140). The used sequencing primers were GS5.8 (5629–5648) and GS3.8 (6495–6515).

RT-PCR of RNA

RNA (5 µg) was reverse transcribed in PCR buffer and the total cDNA was amplified by nested PCR as previously described (5). The PCR product (10 µl of the reaction volume) were electrophoresed on 8% PAGE.

PCR of Genomic DNA

Genomic DNA was amplified by nested PCR. The first PCR was performed with 0.2 µg gDNA, 100 pmol of each primer GH5.1 and GH3, 2.5 U of Taq DNA polymerase (Qiagen, Hamburg, Germany), 0.2 mmol/1 of each dNTP in Qiagen PCR buffer with a final volume of 50 µl. The reaction mixture was cycled 30 times (95° C., 60 s; 65° C., 60 s; 72° C., 90 s). An aliquot of this reaction (0.2 µl) was amplified in the nested PCR using the up-stream primer GH5.2 and the down-stream primer GH3.4 or alternatively (for restriction analysis) the sense-primer GH5.7 and the anti-sense primer GH3.7.

Restriction Digest

The 325 bp fragment of GH-1 (5816–6140) containing the complete intron 3 was digested with 20 U MvnII or with 20 U of N1aIII or with 10 U of DdeI (Boehringer Mannheim, Germany) in a volume of 30 µl containing 10 µl PCR product for 3 hrs. The 1014 bp fragment of GH-1 (5555–6568) containing the genomic sequence from exon 2 to exon 5 was digested with 4 U MaeII (Boehringer Mannheim, Germany) under the same conditions. The fragments were visualized by ethidium bromide staining after run on an 8% PAGE.

Direct Sequencing

PCR products were directly double-stranded sequenced with the Thermo Sequenase cycle sequencing kit containing 7-deaza-dGTP. The reaction was performed according to the manufacture's recommendations (Amersham, Germany). The equencing primers were 5'-labelled with IR-800 fluorescent dye. The products were run under denaturing conditions on a Li-COR DNA automatic sequencer 4200.

Results

Direct sequencing of the PCR-amplified genomic DNA resulted in the detection of a heterozygote point mutation of the first base of the donor splice site of intron 3 in the affected individuals of Families 1, 4 and 5. In detail, we found a G to A transition in Family 1 and the G to C transversion reported previously by us in Families 4 and 5 (5,17). A new splice site mutation with a T to C transition of the second base of the intron 3 donor splice site was detected in Family 2. Restriction fragment analysis of a 327 bp DNA fragment (5816–6140) containing the complete intron 3 with NlaIII (Family 1) and MvnI (Family 2) (FIG. 2), and with DdeI (Families 4 and 5) (5,17) detected the mutation in all affected, but in no unaffected individuals of the 4 families. Ectopic transcript analysis of lymphocyte mRNA was performed in the proband of Family 5 and revealed the presence of a shortened mRNA lacking exon 3 (FIG. 4, lane 1)(5).

Figure 4:
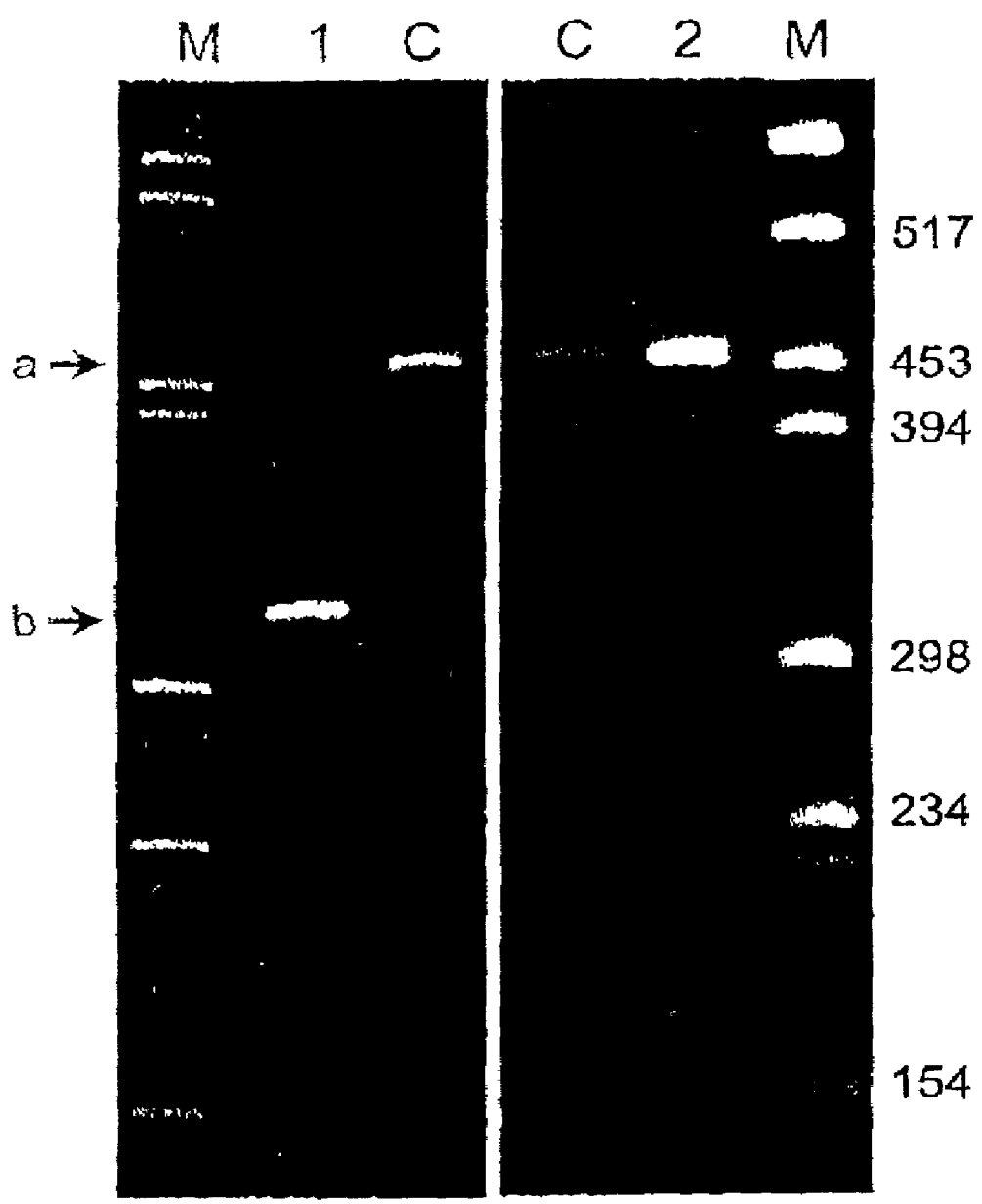
FIG. 4 shows electrophoretic analysis of the amplified GH-1 cDNA. Lane 1 contains the amplified cDNA from a patient with the GH-1 intron 3+1 G to C donor splice site mutation (Family 5) which shows in comparison to the normal control (C) a shortening of the major fragment (arrow b) demonstrating loss of exon 3. The same analysis from one patient with the novel $G^{6191}$ to T missense mutation (V110F) is shown in Lane 2. The main fragment is identical in size to the control's fragment (C) excluding missplicing (arrow a). M=mol wt marker.

In Family 3, we detected a novel heterozygous point mutation in exon 4 with a G to T transversion at position 6191. Co-segregation with GH deficiency were proven by restriction fragment analysis with MaeII demonstrating heterozygote loss of the MaeII recognition site in all affected individuals (FIG. 3). Because the $G^{6191}$ to T mutation was inside an exonic motive that was homologous to a sequence which was reported to act as an exonic splicing enhancer in the human IgM gene (21), we performed ectopic transcript analysis of peripheral lymphocyte RNA. The main GH mRNA fragment found was identical to controls excluding a defect of primary RNA splicing (FIG. 4, lane 2). The missense mutation results in an amino acid exchange from valine to phenylalanine at position 110 of the mutant growth hormone (V110F GH). The alignment of GH sequences revealed that Val 110 is highly conserved in mammalian and also in several non-mammalian GH (FIG. 5).

The clinical characteristics of the affected children at the time of diagnosis are summarized in Table 1.

TABLE 1

Clinical characteristics of 12 children with IGHD II at diagnosis. Quantitative values are given as median and range.

|  |  | Families 1, 2, 4, 5 | Family 3 |
|---|---|---|---|
| Sex | (m/f) | 4/2 | 4/2 |
| Age | (yrs) | 2.3 (0.8 to 7.1) | 6.3 (3.5 to 9.6) |
| Height | (SDscore) | −4.7 (−2.5 to −8.1) | −4.2 (−3.4 to −5.3) |
| Height velocity | (cm/yr) | 4.7 (3.8 to 6.0) | 3.9 (2.5 to 5.0) |
| BMI | (SDscore) | −0.5 (−1.5 to 3.3) | −0.3 (−1.7 to 0.8) |
| Bone age | (yrs) | 0.8 (0.2 to 5.5) | 4.5 (1.5 to 8.0) |

Figure 6:
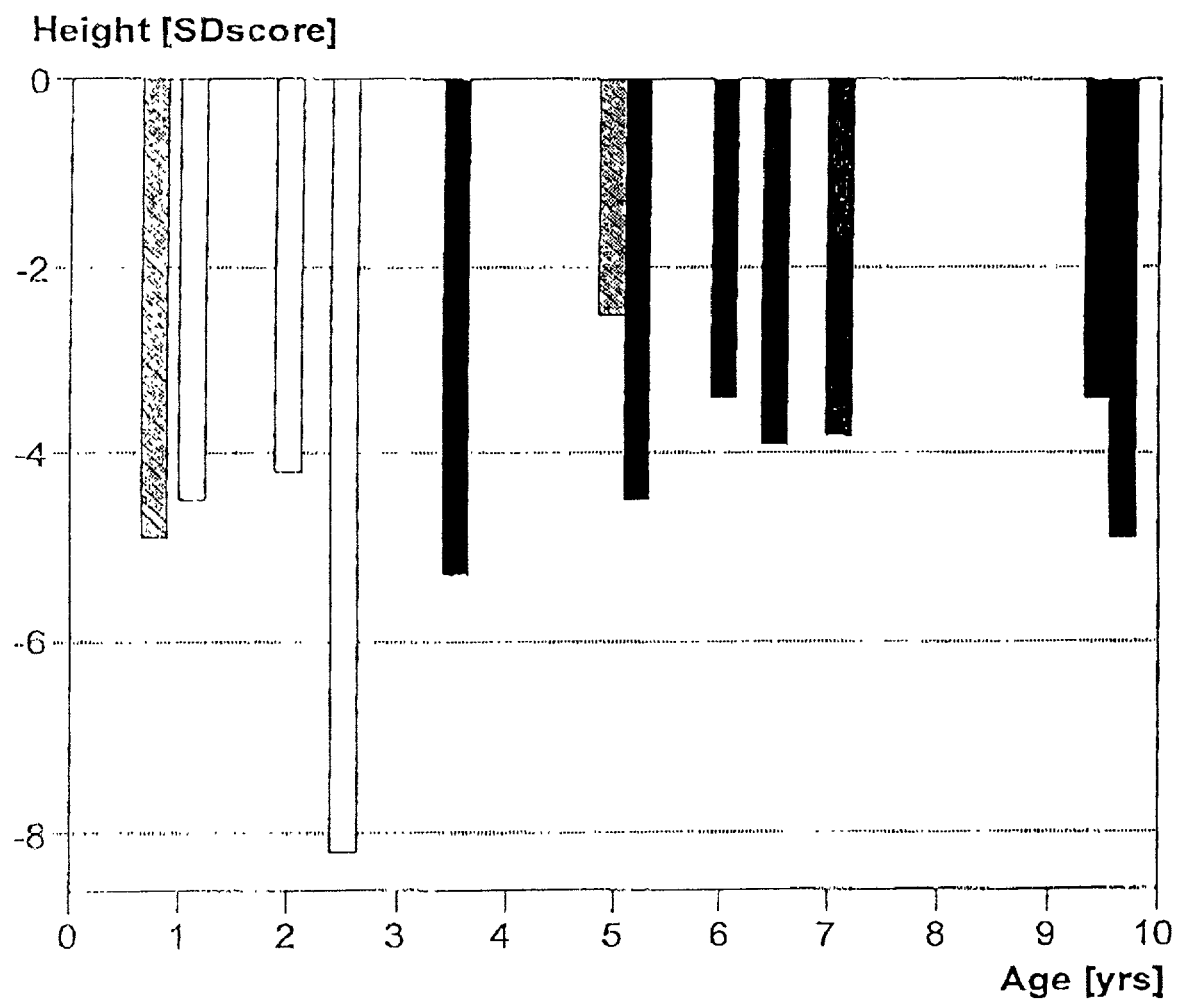
FIG. 6 is a comparison of age and height SDscore at diagnosis of the 12 children with IGHD II. The bars showing data from siblings have the same filling. The black bars show the data from the family with V 110F GH. The high variability of growth failure in IGHD II, even within the same family, is clearly demonstrated.

The SDscores were taken from Prader et al. (22). For better comparison of the genotype-phenotype-relation, the clinical data from the children with GH-1 splice site mutations (Families 1, 2, 4 and 5) and from the children affected by the GH-1 missense mutation (Family 3) are shown separately. The age at diagnosis and the degree of short stature were very variable in members of the same family as illustrated in FIG. 6. Overall, children with GH-1 splice site mutations showed a tendency to an earlier onset and more severe degree of growth failure in comparison to the children with the GH-1 missense mutation (Table 1 and FIG. 6). Only two of the 12 affected children (5.1 and 7.1 years old) were overweight with a BMI SDscore of 2.2 and 3.3. The bone age was retarded in median by 1.6 years (range 0.5 to 3.6). The IGF-I and IGFBP3 levels were pathologically low in all affected children (Table 2).

TABLE 2

Serum levels of the GH dependent factors at diagnosis. Values are given as median and range.

| Age (yrs) | IGF-1 (µg/L) | IGFBP3 (µg/L) | Families 1, 2, 4, 5 (n=) | Family 3 (n=) |
|---|---|---|---|---|
| 0.8–2.5 | 8 (7–26) | 340 (280–400) | 3 | 0 |
| 3.5–6.0 | 14 (10–20) | 860 (740–910) | 1 | 3 |
| 6.5–9.6 | 27 (9–54) | 1150 (990–1410) | 1 | 3 |
| 29.5–58.5 | 48 (31–96) | 775 (540–2670) | 4 | 1 |

The stimulated GH levels were very low in all tested children regardless of the stimulus (Table 3). A GH level above 3 µg/L was reached in 3 of 25 stimulation tests (Table 3).

TABLE 3

Growth hormone peak levels in stimulation tests. Values are given as median and range.

| Stimulus | Peak level (µg/L) | Families 1, 2, 4, 5 (n=) | Family 3 (n=) |
|---|---|---|---|
| Insulin | 1.1 (0.2–5.0) | 5 | 5 |
| Arginine | 0.6 (0.1–2.1) | 6 | 0 |
| Clonidine | 1.7 (0.1–4.3) | 2 | 2 |
| GHRH | 2.1 (0.9–2.3) | 3 | 0 |
| Glucagon | 0.8 (0.5–1.0) | 2 | 0 |

Therapy with 0.17 mg/kg rhGH sc weekly has been performed in 10 children for more than two years. The median height velocity during the first 2 years of therapy increased to 10, 0 cm/year (range 7.0 to 12.5) which was equivalent of a median simplification of the growth velocity by 2.1 fold (range 1.7 to 3.6). MR imaging of the hypophysis showed normal morphology and normal adenohypophysal height according to Argyropoulou et al. (23) in 2 affected children from Families 2 and 5 (−0.5 and −0.6 SDS) and a normal hypophysis with mildly reduced height in 2 children from Families 1 and 2 (−2.5 and −2.6 SDS) and in one adult (Family 1). The 5 affected adults with GH-1 splice site mutations (4 females) had short stature −3.6 (−2.7 to −4.2), centripetal obesity, muscular hypotrophy, but normal fertility. The IGF-I serum levels were severely reduced (Table 2). The mother with V110F GH had short normal stature (−1.8 SDS), but also centripetal obesity and muscular hypotrophy. Her seven pregnancies were reportedly uneventful.

Discussion

All affected individuals of the five families whose pedigrees suggested an autosomal dominant transmission of IGHD carried a deleterious point mutation of GH-1 suggesting a very high prevalence of these mutations in IGHD II. One novel splice site mutation found in one family affected the highly conserved second base of the intron 3 donor splice site (+2T to C). The predicted effect of this mutation as it was shown for mutations of the first base of intron 3 is the skipping of exon 3 during splicing (4,5). The resultant del32-71 GH exerts a dominant negative effect on the wild-type GH which is cell-specific and not observed in non-secretory cell types like EBV-transformed lymphocytes (7) or COS-cells (8,9). Heterodimer formation between wild-type GH and del32-71 GH which lacks one cysteine at position 53 was the first hypothetical proposal for the dominant negative effect (4). This theory has recently been questioned by the finding that the recombinant double mutant del32-71,C165A GH which lacks the unpaired cysteine at position 165 had the same effect in-vitro (9). Both, del32-71 GH and wild-type GH do not accumulate in neuroendocrine cell lines indicating a decrease in intracellular stability (9) whose molecular basis is still unknown (24). In this context, it is of importance that missense mutations of the GH-1 also result in a mutaul GH with a dominant negative effect.

The present inventors report for the first time the V110F mutation of GH-1. Its genetic basis is a C to T transition in a CpG dinucleotide which is a general hotspot for mutations in vertebrate genomes (25). This mutation changes a valine which is completely conserved in mammalians, and in some amphibians and birds, to phenylalanine. Valine is located next to the N-terminal beginning of the third alpha-helix and integrated in the closely packed core of the four-α-helix-bundle of GH (26). The more bulky phenylalanine at this position is very likely to interfere with the normal folding of GH. Two other GH1 missense mutations which co-segregate with IGHD II were recently reported: P89L and R183H (15, 16). Similar to V110F, both mutations change highly conserved amino acids. Proline 89 forms a kink in the second α-helix of GH which leucine is not able to form (24). Arginine 183 is next to the disulfide bond of cysteine 182 whose formation may be disturbed by the more bulky histidine (24). However, the effect of the two missense mutations in cultured neuro-endocrine cells has not yet been shown.

In the past, screening for GH-1 defects was performed if severe growth failure with a height below −4.5 SDS at diagnosis were present (6). Severe short stature according to this definition was only present in one third of our affected individuals at diagnosis indicating that growth failure in IGHD II is less severe than would be expected. The children with the splice site mutations were younger and shorter at diagnosis than their counterparts with the missense mutation. Moderate growth failure was also reported from the family with the P89L mutation (16). In addition, we observed in the three families in which more than one child was affected a pronounced intrafamilial variability between siblings in both mutation groups with height differences exceeding 3.0 SDscore. This variability in growth did not correlate with the severity of growth hormone or IGF-I deficiency because the hormone levels were very low in all tested subjects including those affected individuals with the highest growth velocity and only minor growth failure. There is no substantial evidence for a course of slow progression of GH deficiency in IGHD II like it was described for the dominantly inherited vasopressin deficiency (24). Other factors than systemic GH- and IGF-I-levels must be responsible for the differences in growth failure. These unknown factors obviously modulate the start and predominance of GH dependent growth. Some of these unknown factors may also be involved in the high variability of growth failure reported in Laron syndrome (27).

Data on the systematic examination of the pituitary anatomy in monogenetic disorders are scarce (29). Approximately 50% of the hormone-producing cells of the anterior pituitary are somatotropic cells (29). Recent MRI observations in children with idiopathic GHD suggested a positive relationship of the volume of the adenohypophysis and the secretory GH capacity (30). This is not the case in IGHD II: the 4 children examined by MRI showed a normal adenohypophysis in 2 cases, mild hypoplasia in the two others. Normal size of the anterior hypophysis was also reported in two children affected with IGHD IA suggesting that the presence of GH is not a pre-requisite for normal size of the adenohypophysis (31). Therefore, the combination of normal or almost normal height of the adenohypophysis in the presence of severe GH and IGF-1 deficiency is highly suggestive of the presence of a causative GH-1 mutation. In such cases, the molecular diagnosis establishes the basis for genetic counselling and for the recommendation of a live-long substitution with GH.

References (1) Pfäffle R, Blankenstein O, Wuller S, Heimann K, Heimann G. 2000 Idiopathic growth hormone deficiency: a vanishing diagnosis? Hormone Res. 53 (Suppl 3); 1–8.

(2) Phillips III S A, Hjelle B, Seeburg P H, Zachmann M. 1981 Molecular basis for familial isolated growth hormone deficiency. Proc Natl Acad Sci USA. 78:6372–6375.

(3) Wajnrajch M P, Gertner J M, Harbison M D, Chua S C Jr, Leibel R L. 1996 Nonsense mutation in the growth honnone-releasing hormone receptor causes growth failure analogous to the little mouse. Nat Genet. 12:88–90.

(4) Cogan 113, Phillips III S A, Sakati N, Frisch H, Schober E, Milner D. 1993 Heterogenous growth hormone (GH) gene mutations in familial GH deficiency. J Clin Endocrinol Metab. 76:1224–1228.

(5) Binder G and Ranke M B. 1995 Screening for growth hormone (GH) gene splice-site mutations in sporadic cases with severe isolated GH deficiency using ectopic transcript analysis. J Clin Endocrinol Metab. 80:1247–1252.

(6) Wagner J K, Eble A, Hindmarsch P C, Mullis P E. 1998 Prevalence of human GH-1 gene alterations in patients with isolated growth hormone deficiency. Ped Res. 43:10 5–110.

(7) Binder G, Brown M, Parks J S 1996 Mechansims responsible for dominant expression of human growth hormone gene mutations. J Clin Endocrinol Metab. 81:4047–4050.

(8) Hayashi Y, Yarnamoto M, Ohmori S, Kamijo T, Ogawa M, Sco H 1999 Inhibition of growth hormone (GH) secretion by a mutant G11–1 gene product in neuroendocrine cells containing secretory granules: an implication for isolated GH deficiency inherited in an autosomal dominant manner. J Clin Endocrinol Metab. 84:2134–2139.

(9) Lee M S, Wajnrajch N T, Kirn S S, et al. 2000 Autosornal dominant growth hormone (GH) deficiency Type II: The del32-71-GH deletion mutant suppresses secretion of wild-type GH, Endocrinology. 141:883–890.

(10) Cogan J D, Ramel, B, Lehto M, et al. 1995 A recurring dominant negative mutation causes autosomal dominant growth hormone deficiency—a clinical research center study. 80:3591–3595.

(11) Cogan J D, Prince M A, Lekhakula S, Bundey S, Futrakul A, McCarthy E M, Phillips S A 3rd. 1997 A novel mechanism of aberrant pre-mRNA splicing in humans. Hum Mol Genet. 6:909–912.

(12) Misarelli C, Herrera L, Mericq V, Carvallo P. 1997 Two different splice site mutations in the growth hormone gene causing autosomal dominant growth hormone deficiency. Hum Genet. 101:113–117.

(13) Hayashi Y, Kamijo T, Yamamoto M, et al. 1999 A novel mutation at the donor splice site of intron 3 of the GH-1 gene in a patient with isolated growth hormone deficiency. Growth Horm IGF Res. 9:434–437.

(14) McCarthy E M, Phillips J A 3rd, 1998 Characteriaztion of an intron splice enhancer that regulates alternative splicing of human GH pre-mRNA. Hum Mol Genet. 7:1491–1496.

(15) Wajnrajch M P, Dannics P, Kim S, Gertner J M, Moshang T, Leibel R L. 1997 Pathophysiology of autosomal dominant GH deficiency [Abstract]. Proc 79th Mect of The Endocrine Society; PO 1–084.

(16) Duquesnov P, Simon D, Netchine 1, et al. Familial isolated growth hormone deficiency with slight height reduction due to a heterozygote mutation in GH gene [Abstract]. Proc 80th Meeting of The Endocrine Society; P02–202.

(17) Massa G G, binder G, Oostdijk W, Ranke M B, Wit J M. 1998 De novo mutations of the growth hormone gene: an important cause of congenital isolated growth hormone deficiency? Eur J Pediatr. 157:272–275.

(18) Blum W F, Albertsson-Wikland K, Rosberg S, Ranke M B. 1993 Serum levels of insulin-like growth factor I (IGF-1) and IGF binding protein 3 (1WBP-3) reflect spontaneous growth hormone secretion. J Clin Endocrinol Metab. 76:1610–1616.

(19) Chomczynski P and Sacchi N. 1987 Single-step method of RNA isolation by acid Guanidinium Thiocyanate-Phenol-Chloroform extraction. Anal Biochem. 162:156–159.

(20) Chen E Y, Liao Y-C, Smith D H, Barrera-Saldana H A, Gelinas R E, Seeburg P H. 1989 The human growth hormone locus: Nucleotide sequence, biology, and evolution. Genomics. 4:479–497.

(21) Watakabe A, Tanaka K, Shimura Y. 1993 The role of exon sequences in splice site selection. Genes Dev. 7:407–418.

(22) Prader A, Largo H R, Molinari L, Issler C. 1989 Physical growth of Swiss children from birth to 20 years of age. Helv Paediat Acta. [Suppl]. 513–3 1.

(23) Argyropoulou M, Perignon F, Brunelle F, Brauner R, Rappaport R, 1991 Height of normal pituitary gland as a function of age evaluated by magnetic resonance imaging in children. Pediatr Radiol. 21:247–249.

(24) Dannies P S. 2000 Protein folding and deficiencies caused by dominant-negative mutants of hormones. Vitam Horm. 58:1–26.

(25) Cooper D N, Krawczak M, Antonorakis S E. 1995 In; Scriver C R, Beaudet A L, Sly W S, Valle D, eds. The metabolic and molecular bases of inherited disease. 7th ed. New York: McGraw-Hill; 259–291.

(26) Ultsch M E, Somers W, Kossiakoff A A, deVos A M. 1994 The crystal structure of affinitymatured human growth hormone at 2 A resolution. J Mol Biol, 236: 286–299.

(27) Wood K A, Savage M O. 1996 Laron syndrome: typical and atypical forms. Baillieres Clin Endocrinol Metab. 10:371–387.

(28) Murray R A, Maheshwari H G, Russell E J, Baumann G. 2000 Pituitary hypoplasia in patients with a mutation in the growth hormone-releasing hormone receptor gene. MNR. 21:685–689.

(29) Thorner M O, Vance M L, Laws E F, Horvath E, Kovacs K. 1998 The anterior pituitary. In: Wilson J D, Foster D, Kronenberg F A I, Larsen P R, eds. William's Textbook of Endocrinology. 9th ed, Philadelphia: ViB Saunders; 256.

(30) Hamilton J, Blaser S, Daneman D. 1998 MR imaging in idiopathic growth hormone deficiency. AM. 19:1609–1615.

(31) Zucchini S, Ambrosetto P, Baroncini C, Cacciari E. 1996 Normal pituitary size in two patients with growth hormone gene deletion. J Ped Endocrinol Metab. 9:545–548.

The invention claimed is:

1. A method for diagnosis of autosomal dominantly inherited isolated GH deficiency (IGHD II) in a patient, comprising directly analyzing a nucleic acid sample provided from the patient for the presence or absence of a T at nucleotide position 6191 in exon 4 of the GH-1 gene, and determining that the patient from which the sample is provided has autosomal inherited IGHD II when a T is present at nucleotide position 6191 in exon 4 of the GH-1 gene.

2. A method according to claim 1, also comprising analyzing the sample for the presence or absence of a GH-1 splice site mutation causing skipping of exon 3 of the GH-1 gene.

3. A method according to claim 2, wherein the splice site mutation is +2T to C transition of the second base of the intron 3 donor splice site.

4. A method according to claim 1, wherein the sample is from a patient having a normal size of adenohypophysis.

5. A method according to claim 1, wherein the directly analyzing step comprises amplifying the GH-1 gene or fragments derived from the GH-1 gene.

6. A method according to claim 5, wherein intron 3 and/or exon 2–5 are amplified.

7. A method according to claim 5, wherein the amplifying step comprises PCR amplification of the GH-1 gene and nested PCR of overlapping constituent fragments of the GH-1 gene.

8. A method according to claim 1, wherein the directly analyzing step comprises restriction enzyme digesting amplified fragments.

9. A method according to claim 5, wherein the directly analyzing step further comprises sequencing of amplified fragments.

10. A method according to claim 7, wherein the amplifying step is conducted with one or more specific GH-1 primer pairs wherein the primers are selected from the group consisting of GH3.2 (nt 6578–6600), of the GH1 gene GH5.1 (nt 5503–5525); of the GH1 gene GH5.2 (nt 5555–5577), of the GH1 gene GH3.4 (nt 6547–6568); of the GH1 gene GH5.7 (nt 5816–5835), of the GH1 gene and GH3.7 (nt 6121–6140) of the GH1 gene.

11. A method according to claim 9, wherein the sequencing is conducted with the sequencing primers GS5.8 (nt 5629–5648), of the GH1 gene and GS3.8 (nt 6495–6515) of the GH1 gene.

12. A method according to claim 8, wherein the digesting is conducted with one or more of the restriction enzymes MvnII, NIaIII, DdeI, and MaeII.

13. A method according to claim 2, wherein the directly analyzing step comprises amplifying the GH-1 gene or fragments derived from the GH-1 gene.

14. A method according to claim 3, wherein the directly analyzing step comprises amplifying the GH-1 gene of the patient from which the sample is obtained or fragments derived from the GH-1 gene.

15. A method according to claim 6, wherein the amplifying step comprises PCR amplification of the GH-1 gene and nested PCR of overlapping constituent fragments of the GH-1 gene.

16. A method according to claim 13, wherein the amplifying step is conducted with one or more specific GH-1 primer pairs wherein the primers are selected from the group consisting of GH3.2 (nt 6578–6600), of the GH1 gene GH5.1 (nt 5503–5525); of the GH1 gene GH5.2 (nt 5555–5577), of the GH1 gene GH3.4 (nt 6547–6568); of the GH1 gene GH5.7 (nt 5816–5835), of the GH1 gene and GH3.7 (nt 6121–6140) of the GH1 gene.

17. A method according to claim 15, wherein the amplifying step is conducted with one or more specific GH-1 primer pairs wherein the primers are selected from the group consisting of GH3.2 (nt 6578–6600), of the GH1 gene GH5.1 (nt 5503–5525); of the GH1 gene GH5.2 (nt 5555–5577), of the GH1 gene GH3.4 (nt 6547–6568); of the GH1 gene GH5.7 (nt 5816–5835), of the GH1 gene and GH3.7 (nt 6121–6140) of the GH1 gene.

* * * * *

UNITED STATES PATENT AND TRADEMARK OFFICE
CERTIFICATE OF CORRECTION

PATENT NO. : 7,041,450 B2
APPLICATION NO. : 10/137578
DATED : May 9, 2006
INVENTOR(S) : Michael Ranke It is certified that error appears in the above-identified patent and that said Letters Patent is hereby corrected as shown below:

Claim 10, column 12, lines 59-63, change:

"GH3.2 (nt 6578-6600), of the GH1 gene GH5.1 (nt 5503-5525); of the GH1 gene GH5.2 (nt 5555-5577), of the GH1 gene GH3.4 (nt 6547-6568); of the GH1 gene GH5.7 (nt 5816-5835), of the GH1 gene and GH3.7 (nt 6121-6140) of the GH1 gene." to --GH3.2 (nt 6578-6600 of the GH1 gene), GH5.1 (nt 5503-5525 of the GH1 gene); GH5.2 (nt 5555-5577 of the GH1 gene), GH3.4 (nt 6547-6568 of the GH1 gene); GH5.7 (nt 5816-5835 of the GH1 gene), and GH3.7 (nt 6121-6140 of the GH1 gene).--.

Claim 11, column 12, lines 65-67, change:

"(nt 5629-5648), of the GH1 gene and GS3.8 (nt 6495-6515) of the GH1 gene." to

--(nt 5629-5648 of the GH1 gene), and GS3.8 (nt 6495-6515 of the GH1 gene).--.

Claim 16, column 14, lines 2-6, change:

"GH3.2 (nt 6578-6600), of the GH1 gene GH5.1 (nt 5503-5525); of the GH1 gene GH5.2 (nt 5555-5577), of the GH1 gene GH3.4 (nt 6547-6568); of the GH1 gene GH5.7 (nt 5816-5835), of the GH1 gene and GH3.7 (nt 6121-6140) of the GH1 gene." to --GH3.2 (nt 6578-6600 of the GH1 gene), GH5.1 (nt 5503-5525 of the GH1 gene); GH5.2 (nt 5555-5577 of the GH1 gene), GH3.4 (nt 6547-6568 of the GH1 gene); GH5.7 (nt 5816-5835 of the GH1 gene), and GH3.7 (nt 6121-6140 of the GH1 gene).--.

UNITED STATES PATENT AND TRADEMARK OFFICE
CERTIFICATE OF CORRECTION

PATENT NO. : 7,041,450 B2
APPLICATION NO. : 10/137578
DATED : May 9, 2006
INVENTOR(S) : Michael Ranke Page 2 of 2

It is certified that error appears in the above-identified patent and that said Letters Patent is hereby corrected as shown below:

Claim 17, column 14, lines 10-14, change:

"GH3.2 (nt 6578-6600), of the GH1 gene GH5.1 (nt 5503-5525); of the GH1 gene GH5.2 (nt 5555-5577), of the GH1 gene GH3.4 (nt 6547-6568); of the GH1 gene GH5.7 (nt 5816-5835), of the GH1 gene and GH3.7 (nt 6121-6140) of the GH1 gene." to --GH3.2 (nt 6578-6600 of the GH1 gene), GH5.1 (nt 5503-5525 of the GH1 gene); GH5.2 (nt 5555-5577 of the GH1 gene), GH3.4 (nt 6547-6568 of the GH1 gene); GH5.7 (nt 5816-5835 of the GH1 gene), and GH3.7 (nt 6121-6140 of the GH1 gene).--.

Signed and Sealed this

Third Day of October, 2006

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 14
<212> TYPE: PRT
<213> ORGANISM: Human

<400> SEQUENCE: 1

Gly Ala Ser Asp Ser Asn Val Tyr Asp Leu Leu Lys Asp Leu
1               5                   10

<210> SEQ ID NO 2
<211> LENGTH: 13
<212> TYPE: PRT
<213> ORGANISM: Rat

<400> SEQUENCE: 2

Gly Thr Ser Asp Arg Val Tyr Glu Lys Leu Lys Asp Leu
1               5                   10

<210> SEQ ID NO 3
<211> LENGTH: 13
<212> TYPE: PRT
<213> ORGANISM: Ovine
```

-continued

```
<400> SEQUENCE: 3

Gly Thr Ser Asp Leu Val Tyr Glu Lys Leu Lys Asp Leu
1               5                   10

<210> SEQ ID NO 4
<211> LENGTH: 13
<212> TYPE: PRT
<213> ORGANISM: Porcine

<400> SEQUENCE: 4

Gly Thr Ser Asp Arg Val Tyr Glu Lys Leu Lys Asp Leu
1               5                   10

<210> SEQ ID NO 5
<211> LENGTH: 13
<212> TYPE: PRT
<213> ORGANISM: Bovine

<400> SEQUENCE: 5

Gly Thr Ser Asp Arg Val Tyr Glu Lys Leu Lys Asp Leu
1               5                   10

<210> SEQ ID NO 6
<211> LENGTH: 13
<212> TYPE: PRT
<213> ORGANISM: Chicken

<400> SEQUENCE: 6

Gly Thr Ser Asp Arg Val Phe Glu Lys Leu Lys Asp Leu
1               5                   10

<210> SEQ ID NO 7
<211> LENGTH: 13
<212> TYPE: PRT
<213> ORGANISM: Bullfrog

<400> SEQUENCE: 7

Gly Asn Ile Asp Arg Val Tyr Asp Arg Leu Arg Asp Leu
1               5                   10
```